United States Patent [19]

Ichikawa et al.

[11] Patent Number: 4,735,832

[45] Date of Patent: Apr. 5, 1988

[54] CONTAINER MADE OF SYNTHETIC RESIN AND METHOD FOR MANUFACTURE THEREOF

[75] Inventors: Toshiji Ichikawa, Chofu; Yoshimitsu Asada; Ken Tatebe, both of Tokyo; Tooru Takahashi, Fujinomiya; Juuro Aoyagi, Tokyo; Takeshi Shimomura, Fuji, all of Japan

[73] Assignee: Terumo Kabushiki Kaisha, Tokyo, Japan

[21] Appl. No.: 18,051

[22] Filed: Feb. 24, 1987

Related U.S. Application Data

[63] Continuation-in-part of Ser. No. 731,962, May 8, 1985, abandoned.

[30] Foreign Application Priority Data

May 11, 1984 [JP] Japan .......................... 59-92933
May 11, 1984 [JP] Japan .......................... 59-92934
May 11, 1984 [JP] Japan .......................... 59-92935
May 11, 1984 [JP] Japan .......................... 59-92936

[51] Int. Cl.$^4$ .............. B65D 23/08; B65D 23/02; B32B 13/12; B05D 3/06
[52] U.S. Cl. ......................... 428/35; 428/447; 428/451; 427/2; 427/40; 215/1 C; 215/247; 220/454; 220/455
[58] Field of Search .............. 428/35, 447, 451; 427/2, 39, 40; 215/1 C, DIG. 6, 247; 220/454, 455

[56] References Cited

U.S. PATENT DOCUMENTS

| | | | |
|---|---|---|---|
| 3,136,440 | 6/1964 | Krug et al. | 215/247 |
| 4,137,365 | 1/1979 | Wydeven et al. | 428/451 |
| 4,243,720 | 1/1981 | Schroeter et al. | 428/454 |
| 4,444,973 | 4/1984 | Schönfelder et al. | 428/447 |
| 4,504,549 | 3/1985 | Pines et al. | 428/447 |
| 4,533,369 | 8/1985 | Okita | 427/40 |
| 4,552,791 | 11/1985 | Hahn | 428/35 |
| 4,587,136 | 5/1986 | White et al. | 428/447 |
| 4,686,124 | 8/1987 | Onohara et al. | 428/447 |

Primary Examiner—John E. Kittle
Assistant Examiner—James J. Seidleck
Attorney, Agent, or Firm—Frishauf Holtz Goodman & Woodward

[57] ABSTRACT

A container made of synthetic resin and provided at one portion thereof with at least one tightly closable opening, which container has on a surface thereof a continuous coating having a gas barrier characteristic comprising low permeability to oxygen and carbon dioxide by the plasma treatment reaction of a mixture of a silicon compound having the general formula I with a silicon compound having the general formula II:

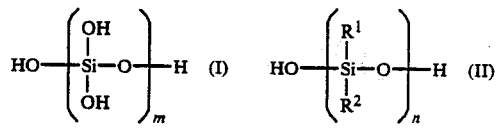

wherein $m=1-5$, $n=1-5$, $R^1$ and $R^2$ are $C_1$-$C_5$ alkyl, $C_1$-$C_5$ alkoxy or phenyl or OH.

39 Claims, 4 Drawing Sheets

POLYETHYLENE SUBSTRATE

FIG.10B

SILICONE COATED POLYETHYLENE SUBSTRATE (NO PLASMA)

FIG.10C

SILICONE COATED POLYETHYLENE SUBSTRATE WITH PLASMA

CONTAINER MADE OF SYNTHETIC RESIN AND METHOD FOR MANUFACTURE THEREOF

This is a continuation-in-part of application Ser. No. 731,962, filed May 8, 1985, which is abandoned.

BACKGROUND OF THE INVENTION

1. Field of the Invention

This invention relates to a container made of synthetic resin and to a method for the manufacture thereof. Particularly, this invention relates to a container made of synthetic resin possessing an extremely high gas barrier property and satisfactory transparency and the ability to retain the interior thereof under a high degree of vacuum or pressure stably for a long period of time and to a method for the manufacture of the container. More particularly, this invention relates to a container for holding a gas containing beverage, a blood collecting vessel under a vacuum, a container for holding a chemical agent, or a container for performing a test and to a method for the manufacture of such a container.

2. Description of the Prior Art

Heretofore, containers made of various types of synthetic resins have been in use in various fields. Among these containers are counted those which by nature are used with the interiors thereof kept under a vacuum or a pressure. Containers for gas containing beverages such as beer, cola, and cider are concrete examples. Some of the containers made of synthetic resin are used for holding chemical solutions. Containers for holding transfusion fluids such as fatty transfusion fluid, nutritive drinks containing amino acids, aqueous glucose solution, and physiological saline are concrete exmaples.

When blood is collected from a human body, the method of vacuum blood collection has found popular acceptance because it entails hemolysis and coagulation only to a minimal extent, warrants collection of specimens suffering from contamination or evaporation of water, and, in terms of efficiency, enables preparation for blood collection and management of devices to be simplified. The vacuum blood collecting vessel which is used in the method of vacuum blood collection comprises a tubular container and a pierceable tightly sealing rubber plug. The tightly sealed container has the interior thereof kept in a vacuum. Desired blood collection with this tightly sealed container is attained by having one end of a blood collection needle plunged into the blood vessel and the other end thereof plunged through the rubber plug into the tightly sealed container thereby establishing communication between the interior of the container and the blood vessel and causing the blood to flow into the container by virtue of the negative pressure present therein. In one example of the vacuum blood collecting vessel heretofore in use, a tubular container made of glass which lacks permeability to gas and excels in transparency is used as the tubular container and a plug made of butyl rubber which is insignificantly permeable to gas and pierceable is used as the plug.

Heretofore, a testing device formed by placing a testing chemicals in a container has been used for effecting desired diagnosis by culturing a microorganism present in blood or some other body fluid or detecting any abnormal component in such blood or body fluid. One example of the testing device comprises a container and a body fluid or gel-like culture medium and an anticoagulant held therein.

In the vacuum container of the nature which has been in use, a container made of glass which lacks permeability to gas and enjoys satisfactory transparency has been adpoted as the container body. The container made of glass, however, has the disadvantage that it is liable to sustain breakage while in storage, transportation, or use and, moreover, is heavy. Thus, researches have been conducted on the feasibility of containers made of light and transparent synthetic resin. Since virtually all grades of synthetic resin are permeable to gas to varying extents, containers made of such synthetic resin are invaded by ambient gas such as, for example, air after prolonged storage. Particularly in the case of the vacuum blood collection tube, it is deprived of its ability to effect required collection of blood after prolonged storage because the inner pressure thereof rises owing to the invasion by the ambient gas. Thus, it has been necessary for the tube to be preserved in a vacuum packaged container. The preservation by the use of the vacuum packaged container, however, proves extremely expensive because this container by nature is required to keep the interior thereof under a high degree of vacuum. This container also has the disadvantage that since it is sealed and opened at the expense of much time and labor, it proves quite costly. Then, in the case of the container for a beverage containing carbon dioxide gas, there is the possibility that the carbon dioxide gas component in the beverage will penetrate the wall of the container and diffuse into the ambient air. In the case of the container for a fatty transfusion fluid or an amino acid, the fluid within is degenerated by oxidation with the oxygen contained in the ambient air entering the container. Thus, the adoption of the container made of synthetic resin makes it necessary for this container to be preserved in a vacuum packaged container. The preservation by the use of the vacuum packaged container, however, proves extremely expensive because this container by nature is required to keep the interior thereof under a high degree of vacuum. This container also has the disadvantage that since it is sealed and opened at the expense of much time and labor, it proves quite costly. In the case of the container for an aqueous solution such as aqueous glucose solution or physiological saline solution, there is the disadvantage that since the water within vaporizes and, in the form of steam, penetrates the synthetic resin wall of the container, the aqueous solution suffers from gradual change of concentration.

Further, such plastic container contained chemical solutions, similarly to the conventional containers, are required to undergo sterilization before they are used. Generally the sterilization of such plastic containers is carried out in saturated steam at an elevated temperature. This treatment is called "high-pressure steam sterilization". Even in the case of the container made of a plastic material such as polyvinyl chloride which has low permeability to gas at normal room temperature, when it is subjected to the high-pressure steam sterilization, the permeability of the plastic material is heightened possibly to a point where the oxygen in the atmosphere penetrates the wall of the container of plastic material and causes degeneration of the solution held therein. When the solution is a highly concentrated amino acid transfusion fluid containing tryptophan or a fatty emulsion for transfusion which contains a component susceptible of degeneration by oxygen, the container has a strong possibility of yielding its content to degeneration. There is further the disadvantage that under the ordinary high-pressure steam sterilization, plastic containers are liable to sustain breakage.

In the case of the testing device, there is the disadvantage that the testing chemicals held within are susceptible to degeneration. When the container make of synthetic resin holds a readily oxidizable chemical solution such as, for example, a liquid or gel-like culture medium or an anticoagulant, this chemical solution is degenerated by oxidation with the oxygen contained in the ambient air which enters the container through its wall. Thus, the adoption of this container made of synthetic reain makes it necessary for the container to be preserved within a vacuum packaged container. The preservation by the use of the vacuum packaged container, however, proves extremely expensive because this container by nature is required to keep the interior thereof under a high degree of vacuum. This container also has the disadvantage that since it is sealed and opened at the expense of much time and labor, it proves quite costly. When the aforementioned testing chemical is an aqueous solution, there is the disadvantage that since the water held within vaporizes and, in the form of steam, finds its way through the wall of the container made of synthetic resin, the concentration of the aqueous solution varies with elapse of time.

An object of this invention, therefore, is to provide a novel container made of synthetic resin of repressed permeability to gas and intended to hold its content under a high degree of vacuum or pressure and a method for the manufacture of the container.

Another object of this invention is to provide a container made of synthetic resin which possesses a high gas barrier property and satisfactory transparency and the ability to retain its content under a high degree of vacuum or pressure stably for a long period of time and a method for the manufacture of the container.

Yet another object of this invention is to provide a vacuum or pressure container made of transparent synthetic resin having no possibility of sustaining breakage and possessing an extremely high gas barrier property and a method for the manufacture of the container.

Still another object of this invention is to provide containers made of synthetic resin and used for holding bicarbonate type beverages, vacuum blood collecting vessel, chemical agent containers, and testing devices and a method for the manufacture of such containers.

SUMMARY OF THE INVENTION

The various objects of the invention described above are accomplished by a container made of synthetic resin and provided at one portion thereof with at least one tightly closable opening, which container has on at least either of the inner and outer surfaces thereof a continuous coating having a gas barrier characteristic comprising low permeability to oxygen and carbon dioxide by the plasma treatment reaction of a mixture of a silicon compound having the general formula I:

wherein m denotes an integer of the value of 1 to 5, with a silicon compound having the general formula II:

wherein n denotes an integer of value of 1 to 5 and $R^1$ and $R^2$ independently denote an alkyl or alkoxy group having 1 to 4 carbon atoms, a phenyl group, or a hydroxyl group, providing that both $R^1$ and $R^2$ are not both hydroxyl group.

This invention also resides in a container made of synthetic resin having the ratio of said compound (II) of 0.5 to 3 mols per mol of said silicon compound (I).

This invention also resides in a container made of synthetic resin having the container body made of transparent synthetic resin. This invention further resides in a container made of synthetic resin having the coating made of a transparent layer. This invention resides in a container made of synthetic resin having the coating formed in a thickness in the range of 0.01 to 2.0 μm. This invention also resides in a container made of synthetic resin satisfying the general formula I on condition that the symbol m denotes an integer of the value of 1 to 5 and the general formula II on condition that the symbol n denotes an integer of the value of 1 to 5 and the symbols $R^1$ and $R^2$ denote an alkyl group having 1 to 4 carbon atoms or a hydroxyl group and wherein said ratio of silicon compound (II) is from 1 to 2 mols per mol of said silicon compound (I). This invention further resides in a container made of synthetic resin satisfying the general formula II on condition that the symbol $R^1$ denotes an alkyl group having 1 or 2 carbon atoms and the symbol $R^2$ denotes a hydroxyl group.

This invention also resides in a vacuum blood collecting vessel in the form of a container made of a synthetic resin, which container is formed of a tubular memeber having one end thereof closed and the other end thereof opened and a pierceable plug member adapted to close tightly the open end of the tubular member, whereby the inner space of the container is to be retained under a vacuum.

This invention further resides in a container holding therein a chemical agent, which is obtained by placing the chemical agent in a container made of synthetic resin through an opening formed in the container and thereafter closing tightly the opening thereby isolating the inner atmosphere of the container from the ambient air.

This invention resides in a testing device, which is obtained by placing a testing agent in a container made of synthetic resin through an opening formed in the container and thereafter closing tightly the opening with a plug member thereby forming a tightly sealed space within the container.

The objects described above are also accomplished by a method for the manufacture of a container made of synthetic resin and provided at one portion thereof with at least one tightly closable opening, which method comprises applying upon at least either of the inner and outer surfaces of the container body a mixed solution containing a silicon compound having the general formula I:

wherein m denotes an integer of the value of 1 to 5, and a silicon compound having the general formula II:

wherein n denotes an integer of the value of 1 to 5 and $R^1$ and $R^2$ independently denote an alkyl or alkoxy group having 1 to 4 carbon atoms, a phenyl group, or a hydroxyl group, drying the applied layer of the mixed solution, and subsequently subjecting the dried layer to a plasma treatment in the absence of a catalyst and in the presence of the gas of oxygen atomcontaining molecule thereby covering the aforementioned surface of the container body with a continuous coating having a gas barrier property characteristics comprising low permeability to oxygen and carbon dioxide.

The various objects described above are accomplished by a method for the manufacture of a container made of synthetic resin and provided at one portion thereof with at least one tightly closable opening, which method comprises applying on at least either of the inner and outer surfaces of the container body a mixed solution containing a silicon compound having the general formula I and a silicon compound having the general formula II by virtue of ultrasonic waves, drying the applied layer of the mixed solution, and subsequently subjecting the dried layer to a plasma treatment in the presence of the gas of an oxygen atom-containing molecule thereby covering the surface of the container body with a continuous coating possessing a gas barrier property.

The various objects described above are further accomplished by a method for the manufacture of a container made of synthetic resin and provided at one portion thereof with at least one tightly closable opening, which method comprises cleaning the surfaces of the container body, then applying upon at least either of the inner and outer surfaces of the container body a mixed solution containing a silicon compound having the general formula I and a silicon compound having the general formula II, drying the applied layer of the mixed solution, and subsequently subjecting the dried layer to a plasma treatment in the presence of the gas of an oxygen atom-containing molecule thereby covering the aforementioned surface of the container body with a continuous coating possessing a gas barrier property.

The aforementioned various objects are accomplished by a method for the manufacture of a container made of synthetic resin and provided at one portion thereof with at least one tightly closable opening, which method comprises cleaning the surfaces of the container body, then applying upon at least either of the inner and outer surfaces of the container body a mixed solution containing a silicon compound having the general formula I and a silicon compound having the general formula II by virtue of ultrasonic waves, drying the applied layer of the mixed solution, and subsequently subjecting the dried layer to a plasma treatment in the presence of the gas of an oxygen atom-containing molecule thereby covering the surface of the container body with a continuous coating possessing a gas barrier property.

This invention also resides in a method for the manufacture of a container made of synthetic resin, wherein the reaction is carried out under a vacuum in the range of 0.01 to 2.0 Torrs. This invention further resides in a method for the manufacture of a container made of synthetic resin the gas of oxygen atom-containing molecule has an oxygen content in the range of 20 to 100%. This invention consists in a method for the manufacture of a container made of synthetic resin, wherein the reaction temperature is in range of 0° to 150° C. This invention also resides in a method for the manufacture of a container made of synthetic resin satisfying the general formula I on condition that the symbol m denotes an integer of the value of 1 to 5 and the general formula II on condition that the symbol n denotes an integer of the value of 1 to 5 and the symbols $R^1$ and $R^2$ denote an alkyl group having 1 to 4 carbon atoms or a hydroxyl group and wherein said ratio of silicon compound (II) is from 1 to 2 mols per mol of said compound (I). This invention further resides in a method for the manufacture of a container made of synthetic resin satisfying the general formula II on condition that the symbol $R^1$ denotes an alkyl group having 1 or 2 carbon atoms and the symbol $R^2$ denotes a hydroxyl group. This invention pertains to a method for the manufacture of a container made of synthetic resin, wherein the plasma treatment is carried out for a period of 0.1 to 60 minutes. This invention further pertains to a method for the manufacture of a container made of synthetic resin, wherein the synthetic resin is transparent synthetic resin. This invention concerns a method for the manufacture of a container made of synthetic resin wherein the cleaning is carried out in an aqueous alkali solution. This invention further concerns a method for the manufacture of a container made of synthetic resin wherein the cleaning is carried out by virtue of ultrasonic waves.

DESCRIPTION OF THE PREFERRED EMBODIMENT

Figure 1:
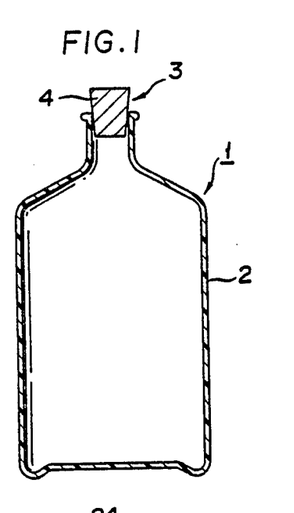
FIG. 1 is a cross sectional view illustrating a typical container made of synthetic resin and produced in accordance with the method of this invention.
Figure 2A:
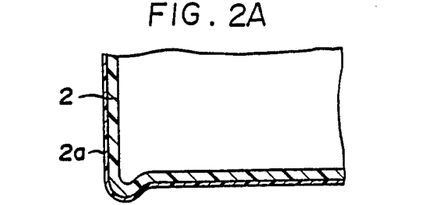
FIGS. 2A–2C are enlarged cross sectional views illustrating in part the container made of synthetic resin illustrated in FIG. 1.
Figure 2B:
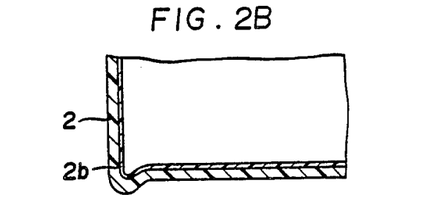
Figure 2C:
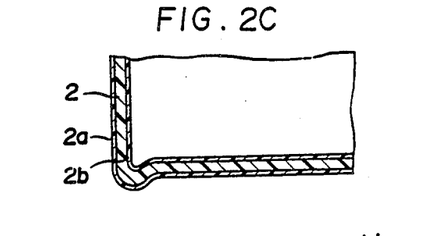
Figure 3:
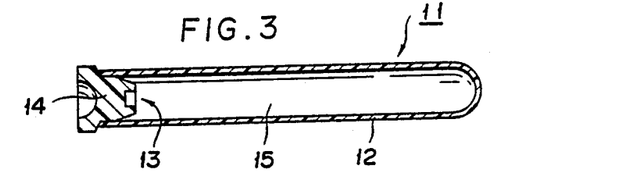
FIG. 3 is a cross sectional view illustrating a typical vacuum blood collecting vessel produced by the method of the present invention.

Now, the present invention will be described in detail below with reference to the accompanying drawings. As illustrated in FIG. 1, a container 1 made of synthetic resin according to the present invention is formed of a container made of transparent synthetic resin and provided at one portion thereof with at least one tightly closable opening 3. On at least either of the inner and outer surfaces of the container body 2 made of transparent synthetic resin, a transparent coating is formed by causing silicon compounds of the general formulas I and II to react with each other by a plasma treatment. As illustrated in FIG. 2A, for example, a transparent coating 2a is formed by the reaction of the silicon compounds throughout on the outer surface of the container body 2. Otherwise, as illustrated in FIG. 2B, the transparent coating 2b is formed throughout on the inner surface of the container body 2. Alternately, as illustrated in FIG. 2C, the transparent coating 2a is formed on the outer surface of the container body 2 and the transparent coating 2b is formed on the inner surface thereof. It should be noted, however, that in FIGS. 2A-2C, the transparent coatings 2a, 2b are drawn in an exaggerated thickness.

Figure 4A:
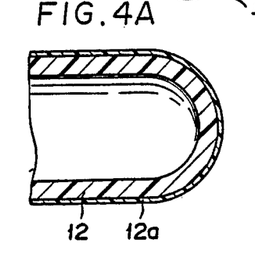
FIGS. 4A–4C are enlarged cross sectional views illustrating in part the vacuum blood collecting vessel illustrated in FIG. 3.
Figure 4B:
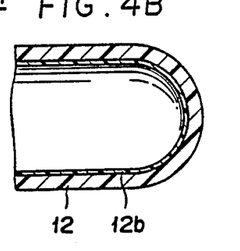
Figure 4C:
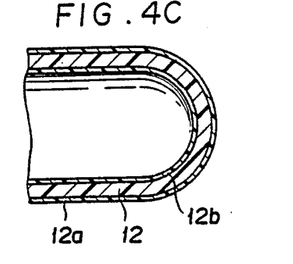

FIG. 3 and FIGS. 4A-4C illustrated another embodiment of this invention in the form of a vacuum blood collecting vessel. A vacuum blood collecting vessel 11 comprises a tubular member 12 made of transparent synthetic resin having one end thereof closed and the other end thereof opened and a pierceable plug member 14 adapted to close tightly the open end 13 of the tubular member 12. In the vacuum blood collecting vessel 11, an empty space 15 enclosed with the tubular member 12 and the plug member 14 is retained in a vacuum or decompression. On at least either of the inner and outer surface of the tubular member 12 made of synthetic resin, the transparent coating is formed by causing the silicon compounds of the general formulas I and II to react with each other by the plasma treatment. As illustrated in FIG. 4A, for example, a transparent coating 12a is formed by the reaction of the silicon compound throughout on the outer surface of the tubular member 12. Otherwise, as illustrated in FIG. 4B, the transparent coating 12b is formed similarly throughout on the inner surface of the tubular member 12. Alternately, as illustrated in FIG. 4C, the transparent coating 12a is formed on the outer surface of the tubular member 12 and the transparent coating 12b is formed on the inner surface thereof. It should be noted, however, that in FIGS. 4A-4C, the transparent coating 12a, 12b are drawn in an exaggerated thickness.

Figure 5:
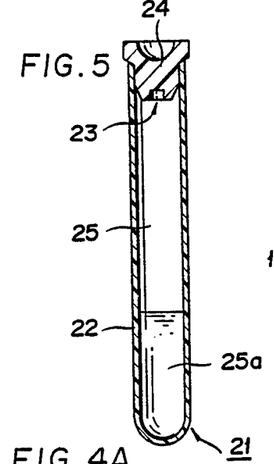
FIG. 5 is a cross sectional view illustrating a typical testing device according with the present invention.
Figure 6A:
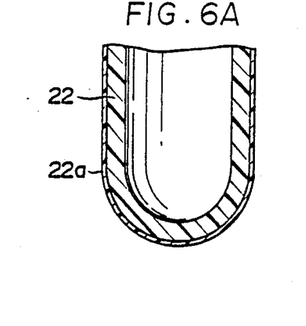
FIGS. 6A–6C are enlarged cross sectional views illustrating in part the testing device illustrated in FIG. 5.
Figure 6B:
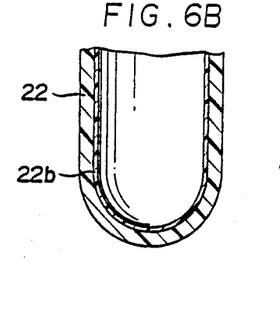
Figure 6C:
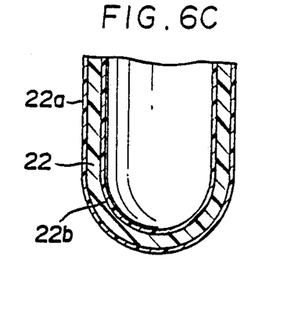

FIG. 5 and FIGS. 6A-6C illustrated yet another embodiment of the present invention is the form of a vacuum-collection type testing device. A testing device 21 comprises a container body 22 made of transparent synthetic resin and provided at one portion thereof with at least one tightly closable opening 23 and a plug member 24 adapted to close tightly the opening 23 of the container body 22. This testing device 21 has a testing agent 25a kept in an empty sapce 25 which occurs within the container body 22. This empty space 25 is desired to be vacuumized or decompressed and held under an atmosphere of a gas inactive to the testing agent. On at least either of the inner and outer surfaces of the container body 22 made of transparent synthetic resin, a transparent coating is formed by the reaction of the silicon compounds of the general formulas I and II by the plasma treatment. As illustrated in FIG. 6A, for example, a transparent coating 22a is formed by the reaction of the silicon compounds throughout on the outer surface of the container body 22. Otherwise, as illustrated in FIG. 6B, the transparent coating 22b is formed similarly throughout on the inner surface of the container body 22. Alternatively, as illustrated in FIG. 6C, the transparent coating 22a is formed throughout on the outer surface of the container body 22 and the transparent coating 22b on the inner surface thereof. It should be noted, however, that in FIGS. 6A-6C, the transparent coatings 22a, 22b are drawn in an exaggerated thickness.

The synthetic resin to be used in the present invention for the formation of the container body or the tubular member is not specifically defined. It is desired to be transparent synthetic resin. To be more specific, it is desired to be a homopolymer or copolymer of styrene, a homopolymer or copolymer of methyl methacrylate, an ethylene-vinyl alcohol copolymer or polyethylene terephthalate. Where the container is required to be resistant to heat, the synthetic resin is desired to be soft or hard vinyl chloride resin, a cross-linked ethylene-vinyl alcohol copolymer, polypropylene, polycarbonate, or a polyester. Styrene polymers embrace copolymers of styrene with other copolymerizable monomers in addition to polystyrene. Examples of the copolymerizable monomer usable for the styrene copolymers include butadiene, methyl methacrylate, and maleic anhydride. Methyl methacrylate polymers embrace copolymers of methyl methacrylate with other copolymerizable monomers in addition to polymetyl methacrylate. Examples of the polycarbonate include the polycarbonates and diethylene glycol bis-allyl carbonate disclosed in U.S. Pat. No. 3,305,502 and Christofer and Fox: "Polycarbonates," pages 161-176 (1962) in addition to such bisphenol type carbonates as 4,4'-isopropylidene diphenol polycarbonate. Most preferable material is polyethylene terephthalate.

One of the two components for the formation of the coating is a silicon compound having the general formula I:

(I)

wherein m denotes an integer of the value of 1 to 5.

The other component is a silicon compound having the general formula II:

(II)

In the general formula II, n denotes an integer of the value of 1 to 5 and $R^1$ and $R^2$ independently denote an alkyl or alkoxy group having 1 to 4 carbon atoms, phenyl group, or hydroxyl group. It is provided, however, that both $R^1$ and $R^2$ do not simultaneously denote a hydroxyl group. Preferably, $R^1$ and $R^2$ independently denote an alkyl group having 1 to 4 carbon atoms or a hydroxyl group, providing that both $R^1$ and $R^2$ do not simultaneously denote a hydroxyl group. Particularly, the silicon compound proves most desirable when $R^1$ is an alkyl group having 1 or 2 carbon atoms and $R^2$ is a hydroxyl group. The amount of the silicon compound of the general formula II to be used is required to fall in the range of 0.5 to 3 mols, preferably 1 to 2 mols, per mol of the silicon compound of the general formula I.

The above-mentioned silicon compounds (I) and (II) may be prepared by dissolving organoalkoxy silanes such as tetraalkoxy silanes (e.g., tetramethoxy silane, tetraethoxy silane, tetraisopropoxy silane, etc.) and alkyl trialkoxy silanes (e.g., methyl trimethoxy silane, methyl triethyl silane, methyl triisopropoxy silane, etc.) into an organic solvent such as methanol, ethanol, isapropanol and butanols and adding water in an amount of 30 to 200%, preferably 50 to 110% of water to the alkoxy groups to be hydrolyzed and an acid to control pH to 1–5, preferably 3–4.

These organoalkoxy silanes in the solvent become respectively silicon compounds shown in the general formula I and II by the hydrolysis.

The mixture of the two silicon compounds described above is used in the form of a solution in such an organic solvent as methanol, ethanol, isopropanol, or butanols. The concentration of the mixture in the solution falls in the range of 3 to 50% by weight, preferably 5 to 35% by weight.

The transparent coating is formed as described below. When this coating is to be formed on the outer surface of the container body, for example, the container body, with the opening tightly stoppered, is immersed in the solution of the mixture of the silicon compounds. The duration of this immersion generally falls in the range of 0.1 to 60 minutes, preferably 0.3 to 5 minutes. In this case, application of ultrasonic waves upon the bath of immersion results in improvement in the gas barrier property of the formed coating because the waves accelerate extraction of air from the fine pores on the surface of the container of synthetic resin and entry of the solution into the fine pores. The application of the solution of the mixture on the surface is not limited to the immersion described above. It may be effected by spraying or some other suitable means.

The treatment of immersion described above is carried out at a temperature generally in the range of 0° to 50° C., preferably 10° to 30° C. When this treatment is to be carried out under the influence of ultrasonic waves, it is effected advantageously at a bath temperature in the range of 0° to 50° C., preferably 10° to 30° C., at a frequency in the range of 20 to 200 KHz, preferably 25 to 50 KHz, for a period in the range of 0.1 to 10 minutes, preferably 0.5 to 5 minutes.

The container body on which the solution of the mixture has been applied as described above is dried at a temperature in the range of 50° to 150° C., preferably 60° to 70° C., for period in the range of 3 to 30 minutes, preferably 5 to 15 minutes, and subsequently subjected to a plasma treatment.

Figure 7:
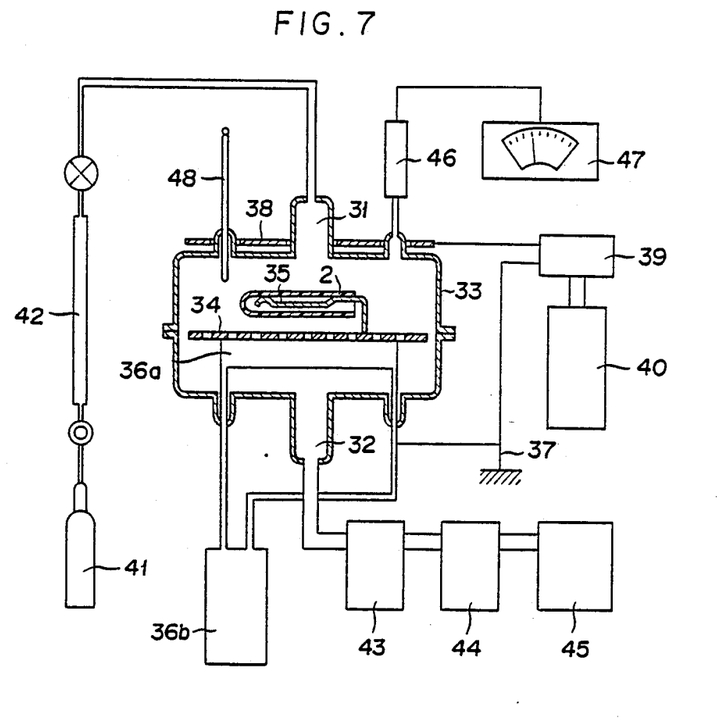
FIG. 7 is a schematic cross sectional view illustrating a typical device for plasma treatment involved in the working of the present invention.

The plasma treatment serve to transform the coating applied on the surface of the container body as described above into a transparent coating. This plasma treatment is carried out as follows. Within a reactor 33 provided with a gas inlet 31 and a gas outlet 32, an electrode 34 is disposed as illustrated in FIG. 7. On this electorde 34, a container body supporting device 35 is disposed. The container body 2 which has the solution of mixture applied on the surface thereof is supported in place by the container body supporting device 35. For exmaple, this supporting of the container body 2 is effected by first removing the plug member from the container body 2 and then allowing the container body supporting device 25 to be inserted into the container body 2. The electorde 34 is adjoined to a cooling device 36a and, at the same time, the cooling device 36a is connected to a temperature regulator 36b to permit circulation therethrough of a coolant such as, for example, water. To the electrode 34 is connected a grounding wire 37. To the electrode 34 is opposed an opposite electrode 38. This opposite electrode 38 is connected through a matching device 39 to a high-frequency power source 40. To the gas inlet are connected an oxygen container 51 and a flowmeter 42. On the other hand, as an oil diffusion pump 44 and an oil rotary pump 45 through the medium of a trap 43. In FIG. 7, the symbol 46 denotes a pressure sensor, the symbol 47 a vacuum gauge, and the symbol 48 a thermometer.

Then, by the operation of the vacuumizing devices such as the oil rotary pump, the atmospheric gas held within the reactor 33 is extracted through the gas outlet 32 until the inner pressure of the reactor 33 is reduced to about 0.05 Torr. Subsequently, the oxygen gas from the oxygen container 41 is supplied via the flowmeter 42 into the reactor 33 through the gas inlet 31 and, at the same time, electric current is passed to the electrode 34 as to irradiate the applied layer of the solution with the plasma consequently generated. In this case, the container body is desired to be rotated around its axis during the course of the irradiation so that the applied layer will be uniformly exposed to the plasma.

In this case, for the plasma reaction to proceed advantageously, the pressure within the reactor is kept in the range of 0.01 to 2.0 Torrs, preferably 0.05 to 0.5 Torr, during the course of the plasma reaction. The electrode 34 serving as a base plate is kept cooled with the coolant circulated through the cooling device 36a. The inner temperature of the reactor is desired to fall in the range of 0° to 150° C., preferably 30° to 70° C. The amount of high-frequency electric power is in the range of 0.05 to 260 W, preferably 0.2 to 100 W. Examples of the gas of oxygen atom-containing molecule include molecular oxygen, ozone, carbon monoxide, carbon dioxide gas, and nitrogen monoxide. The molecular oxygen (hereinafter referred to as "oxygen gas") is a desirable selection. The amount of the oxygen gas to be advantageously used falls in the range of 100 to 800 ml/min., preferably 200 to 500 ml/min. The irradiation of plasma is carried out for a period in the range of 0.1 to 60 minutes, preferably 0.3 to 5 minutes. As the result, otherwise possible elevation of the temperature of the container body as the substrate for irradiation owing to the exposure to the plasma can be precluded. Of course, the plasma treatment can be performed in one round. Otherwise, it may be carried out in a plurality of split rounds such as two rounds, each round lasting for a period in the range of 0.1 to 60 minutes, preferably 0.3 to 10 minutes, so that the container under treatment may be left cooling during the intermissions. This split exposure to the plasma proves advantageous in the sense that undesirable elevation of the temperature of the substrate due to the exposure to the plasma can be avoided. Here, the reaction temperature falls roughly in the range of 40° to 80° C. The transparent coating formed under the reaction conditions described above has a thickness in the range of 0.01 to 2.0 μm, preferably 0.03 to 0.2 μm.

The application of the transparent coating is effected more advantageously when the surface of the container body is cleaned by washing before the solution of the mixture of silicon compounds is applied on said surface. This washing is effected by using water, an aqueous acid solution, an aqueous alkali solution, an alcohol, or an aqueous surfactant solution, for example. Among other solutions, the aqueous alkali solution proves particularly desirable. Concrete examples of the aqueous alkali solution include aqueous solution severally of sodium carbonate, potassium carbonate, lithium carbonate, sodium hydrogen carbonate, sodium hydroxide, and potassium hydroxide. The concentration of the alkali compound in the aqueous solution generally falls in the range of 0.1 to 20% by weight, preferably 1 to 10% by weight. The duration of the washing treatment generally falls in the range of 0.1 to 30 minutes, preferably 2 to 10 minutes. The washing treatment yields better results when it is carried out by virtue of ultrasonic waves. This is probably because the ultrasonic waves clean the fine pores on the surface of the substrate so thoroughly that the solution applied subsequently is allowed to reach the bottoms of the fine pores. This treatment with ultrasonic waves is carried out at a frequency in the range of 20 to 200 KHz, preferably 25 to 50 KHz, for a period in the range of 0.1 to 10 minutes, preferably 0.5 to 5 minutes. Of course, the washing treatment, when carried out by virtue of ultrasonic waves, gives fairly satisfactory results if the solution to be used is other than an aqueous alkali solution. The washing treatment gives the most desirable results when it is carried out with an aqueous alkali solution under the influence of ultrasonic waves.

Then we have studied the coated film formed on the surface of the container made of synthetic resin in accordance with the present invention. Firstly as being clear from infrared absorption charts shown in FIGS. 10A to 10C, OH group in a solution for forming the coating disappeared, so it is considered that coated film having construction of cross-linked silicon compound (organosiloxane) is formed. But although simple cross-linked film has little gas barrier property, the container made of synthetic resin of the present invention has sufficient gas barrier property as shown in Table 1. Thus it is considered that such gas barrier property has relation to alkyl group such as methyl, ethyl, etc. as shown by $R^1$ and $R^2$ present in the silicon compound. Because if $R^1$ and $R^2$ are absent, the film becomes complete vitreous and the glass has sufficient gas barrier property.

Figure 10A:
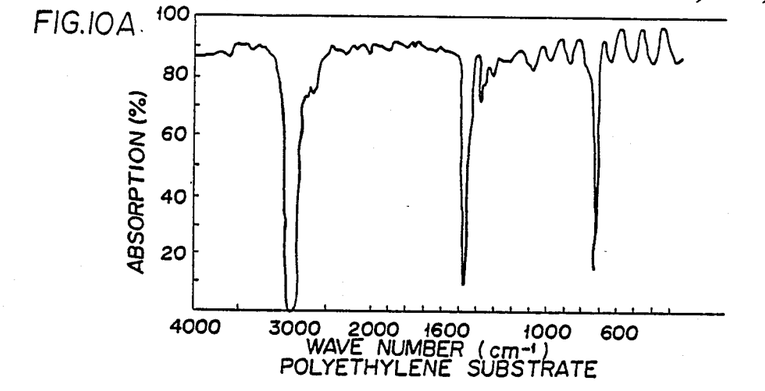
FIG. 10A-10C are infrared absorption spectrum charts of the coated film.
Figure 10B:
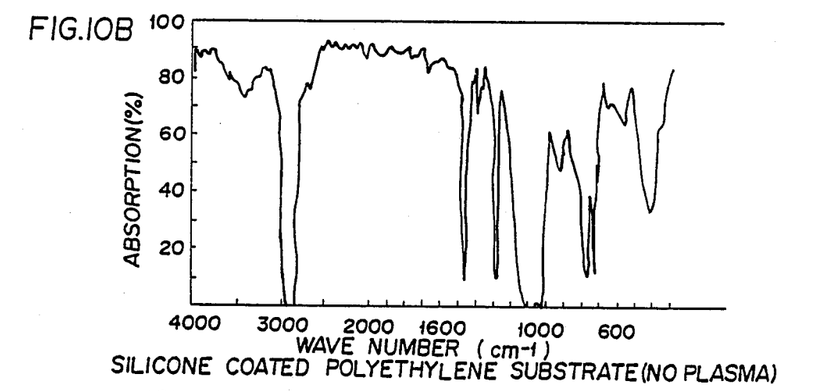
Figure 10C:
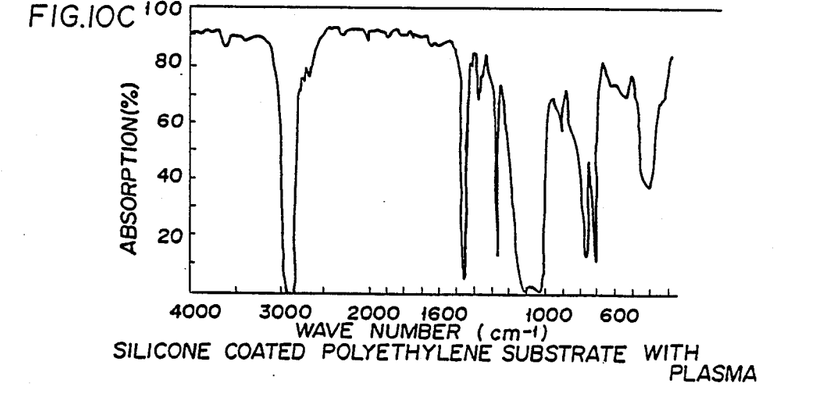

Therefore, it is considered that the coated film formed on the surface of the container made of synthetic resin has a continuous layer of having substantially no $R^1$ and $R^2$ groups. Especially, it is considered that such layer is formed on the surface side of the coated film. The reason is considered that not only OH but also $R^1$ and $R^2$ are apt to be removed from the surface side where plasma is radiated directly by aforementioned plasma treatment. On the contrary, it is considered that $R^1$ and $R^2$ exist at an inner side apart from the surface side, especially a contact surface of the container. Thus methyl group remains as shown in FIGS. 10A to 10C. Therefore, it is considered that the coated film formed on the surface of the container made of synthetic resin in accordance with the present invention has gas barrier property based on the on the surface side and excellent adhesiveness with the container body made of synthetic resin based on $R^1$ and $R^2$ at the contact side with the container body.

The other synthetic resin containers contemplated by the present invention such as, for example, containers for gas containing beverages (such as beer, cola, cider, and juice) and containers for foodstuffs (such as sausages and processed fruits) can be produced in the same manner as described above. The opening formed in each of these containers is tightly closed with a tight plug or lid having a gas barrier property.

The container made of synthetic resin which has been produced by the method described above is put to use as follows. The container body 2 of the container 1 made of synthetic resin as illustrated in FIG. 1 is filled with its content such as a gas containing beverage and, with the interior of the container body kept under a vacuum, under a pressure, or under the atmosphere of an inactive gas, the container 1 is tightly sealed with the plug member 4. The container is then put to use.

When the container is used for holding a chemical agent such as, fatty transfusion fluid or other similar transfusion fluid, a nutritive drink containing amino acids, an aqueous glucose solution, or physiological saline solution, this container is filled with the chemical agent and, with the content kept sealed with a gas such as nitrogen, helium, argon, or carbon dioxide gas which is inactive to the aforementioned chemical agent, the container is tightly sealed with the plug member of a satisfactory gas barrier property.

Similarly to the conventional containers of the class discussed herein, the container which has been filled with the chemical agent and tightly sealed with the plug member must be subjected to sterilization before it is put to use. The treatment of sterilization is generally carried out in the form of high-pressure steam sterilization. This treatment is effected by placing a plurality of such containers filled with their contents in an autoclave adopted for the treatment, evacuating the closed autoclave until the oxygen trapped within the autoclave is substantially completely removed, and introduce steam into the autoclave until saturation. Then, an inactive gas such as, for example, argon, helium, or nitrogen, preferably nitrogen, is introduced into the autoclave until a prescribed pressure, to ready the autoclave for sterilization. The temperature of this sterilization generally falls in the range of 100° to 130° C., preferably 115° to 126° C. The atmosphere for the sterilization is pressed with an inactive gas to a pressure about 10 to 200% (such as, for example, about 0.3 to 0.8 kg/cm²) higher than the pressure of the saturated steam, as absolute pressure, at the temperature of sterilization. Generally, the pressure during the course of the sterilization, as gauge pressure, roughly falls in the range of 1.2 to 2.0 kg/cm². The duration of this sterilization properly falls in the range of 10 to 40 minutes. In the course of the sterilization, the inactive gas is suitably introduced into the autoclave to retain the interior of the autoclave under a prescribed pressure.

In the case of the vacuum blood collecting vessel, the plug is made of butyl rubber or some other similar material. The material thus used is desired to be such that the plug member can be smoothly pierced by a blood collection needle without producing any loose gap between the blood collection needle and the wall of a puncture formed in the plug member owing to the pierce. The material is also desired to possess low permeability to gas. A typical example of the material which meets this description is a combination of a thermoplastic elastomer, polyisobutylene, and a partially cross-linked butyl rubber.

As regards the proportions of the components which make up the combination, the proportion of polyisobutylene is desired to fall in the range of 100 to 200 parts by weight, preferably 120 to 150 parts by weight, and that of the partially cross-linked butyl rubber in the range of 100 to 200 parts by weight, preferably 120 to 150 parts by weight, both based on 100 parts by weight of the thermoplastic elastomer.

Examples of the thermoplastic elastomer include ethylene-propylene rubber type elastomers, polyester elastomers, nylon elastomers, styrene-isopropylene block copolymer, and styrene-butadiene block copolymer. The polyisobutylene is desired to have a molecular weight in the range of 15,000 to 200,000, preferably 80,000 to 150,000. The partially cross-linked butyl rubber is produced by copolymerizing isobutylene with a small amount (0.3 to 3.0 mols, for exmaple) of isoprene and partially cross-linking the resultant butyl rubber.

The vacuum blood collecting vessel so produced is subjected, when necessary, to sterilization by radiation before or after the tube is tightly closed with the plug member. The radiation used for this sterilization is an electromagnetic radiation such as gamma ray or electron beam. The gamma ray is more desirable than the elctron beam. The intensity of the radiation is desired to fall in the range 0.1 to 4 Mrads, preferably 0.5 to 2.5 Mrads.

Figure 8:
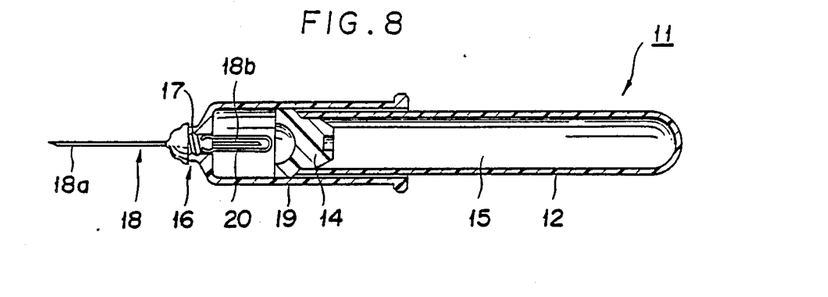
FIG. 8 and FIG. 9 are cross sectional views illustrating modes of use of the vacuum blood collecting vessel.
Figure 9:
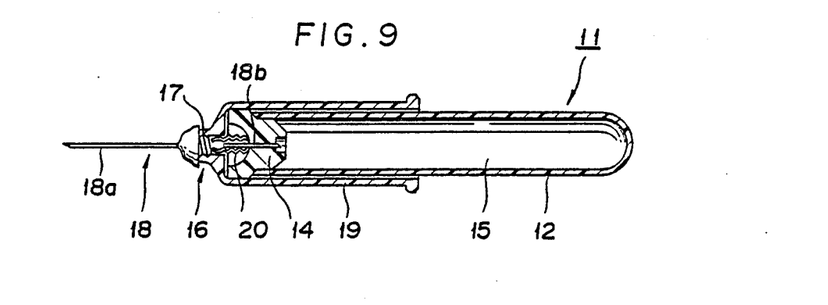

The vacuum blood collecting vessel constructed as described above is put to use as follows. As illustrated in FIG. 8, one end is closed and the other end is opened and the insertion is made through the open end into the threaded hole 17 of the closed end 16. This blood collection needle comprises a blood vessel piercing part 18a and a plug piercing part 18b. The plug piercing part 18b is enveloped with a luer adapter 20 made of synthetic resin. The blood vessel piercing part 18a of the blood collection needle 18 is plunged into the blood vessel such as the vein and the vacuum blood collecting vessel 11 is pressed down into the closed part 16 of a blood collecting vessel holder 19. Consequently, the plug piercing part 18b of the blood collecting vessel 18 penetrates the luer adapter 20 and the plug member 14 and the leading end of the plug piercing part 18b reaches the inner space 15 of the blood collecting vessel 11 as illustrated in FIG. 9, establishing communication between the blood vessel and the inner space 15. By the negative pressure with the aforementioned inner space 15, the blood in the blood vessel flows into the inner space 15 of the blood collection tube 11 in a total volume corresponding to the degree of vacuum existing in the inner space. The blood collection is completed by removing the blood vessel piercing part 18a of the blood collection needle 18 from the blood vessel.

When the container made of synthetic resin illustrated in FIG. 5 is to be used as a testing device, a chemical agent 25A for the test is placed in the container and the inner space 25 of the container is retained under a vacuum or filled with an atmosphere of an inactive gas such as nitrogen, argon, helium, or carbon dioxide gas, with the aforementioned opening 23 tightly closed with the plug member 24.

Examples of the chemical agent for the test include various liquid or gel-like culture media, anticoagulants such as ethylenediamine tetraacetates and sodium oxalate, CPD fluid, and ACD-A fluid.

The plug member 24 used in this case is similar to the plug member 14 in the vacuum blood collecting vessel.

The testing device obtained as described above is sterilized before or after the chemical agent for test is placed therein. The sterilization can be carried out by the use of steam or radiation. The sterilization by radiation is more desirable than that by radiation. The radiation to be used in this case is an electromagnetic radiation such as gamma ray or electron beam. The gamma ray is better selection than the electron beam. The intensity of radiation is desired to fall in the range of 0.1 to 4 Mrads, preferably 0.5 to 2.5 Mrads.

The testing device constructed as described above is used in much the same way as the vacuum blood collecting vessel. In this case, the testing device is used in its unaltered form when the specimen under test or the substrate for culture is anaerobic. When the specimen under test or the substrate for culture is aerobic, then the test or culture is carried out by removing the plug member from the container or by introducing oxygen or air into the interior of the container.

Now, the present invention will be described more specifically below with reference to working examples.

EXAMPLE 1

A container made of polyethylene terephthalate was immersed in an aqueous 2.5% $Na_2CO_3$ solution for 5 minutes (under application of ultrasonic waves). It was then immersed in a solution containing the silicon compound having 50 mol % of tetramethoxy silane and 50 mol % of methyl triethoxy silane containing about 100% of water for hydrolysis of the alkoxy groups in a concentration of 12% by weight in isopropanol (pH about 3.5) at 20° C. for one minute and lifted from the solution at a rate fo 16 cm/minute. Then, the container was dried at 70° C. for 30 minutes. In a low-temperature plasma reaction device, denoted by 33 in FIG. 7, the tube made of a synthetic resin was inserted. The device was evacuated (to 0.05 Torr) and then charged with oxygen gas to a pressure of about 0.3 Torr. The tube was subjected to a plasma treatment at a plasma output power of 100 W, with two parallel plate electrodes (50 mm $\times$ 50 m) separated by a distance of about 50 mm. As the result, a transparent coating 0.1 $\mu$m in thickness was deposited on one surface of the container. To test the coated container for permeability to oxygen and carbon dioxide gas, a film (12 m in thickness and 50 $cm^2$ in area) of the same material as the container was treated by following the procedure described above. By the test with a gas permeation tester made by Lyssy Corp., the resultant coated film was found to pass 50.6 ml of oxygen and 204 ml of carbon dioxide gas per $m^2$ day atm. In the following exmaples, the permeability of the container to gas was tested by similarly preparing a film of the same material as the container involved, subjecting the film to the coating treatment, and subjecting the coated film to test.

EXAMPLE 2

By following the procedure of Example 1, the treatment with ultrasonic waves was performed for five minutes by using a mixed solution of a concentration of 5% by weight. The container was dried at 70° C. for 30 minutes and was immediately subjected to the plasma treatment under the same conditions as in Example 1. Consequently a transparent coating 0.04 μm in thickness was formed. The measurements of permeability similarly determined were 78 and 313 respectively for oxygen and carbon dioxide gas.

CONTROL 1

A container made of the same polyethylene terephthalate, in its untreated form, was tested for permeability to oxygen and carbon dioxide gas. The measurements of permeability similarly determined were 231 and 939 respectively.

CONTROL 2

By following the procedure of Example 1, a container of the same synthetic resin was immersed in a mixed solution having a concentration of 32% by weight for five minutes. The treatment with ultrasonic waves and the treatment with plasma were omitted. Consequently, a transparent coating 0.14 μm is thickness was formed. The measurements of permeability similarly determined were 213 and 854 respectively for oxygen and carbon dioxide gas.

EXAMPLES 3-12

By following the procedure of Example 1, polyethylene terephthalate films 12 μm (Examples 3-7) and 11.5 to 12 μm (Examples 8-12) in thickness were washed in varying treating liquids indicated in Table 1 under application of ultrasonic waves and, thereafter, subjected to a drying treatment. Then, the films were immersed in isopropanol solutions containing the same silicon compounds as used in Example 1 in the concentrations indicated in Table 1 for a fixed duration of four minutes, during which period the films in the solutions were exposed to ultrasonic waves at a frequency of 45 KHz. The films were dried at 70° C. for five minutes. The dried films were subjected to a plasma treatment at varying outputs and for varying periods indicated in Table 1 in the presence of 100% oxygen. The results were as shown in Table 1.

It is noted from the results that the degrees of gas barrier property exhibited by the films decreased in the order of neutral detergent >5% $Na_2CO_3$>alkali-methanol in terms of the kind of agent used for the wasing. This fact implies that the film formed by plasma is affected by the method of film cleaning and the condition of film surface.

TABLE 1

| Example | Pretreating Agent | Time (min) | Drying of Pretreating Temp. (°C.) | Time (min) | Dipping Conc. (%) | Drying Temp. (°C.) | Time (min) | Plasma reaction Power (W) | Time (min) | Gas permeability (ml/m² day atm) $O_2$ | $CO_2$ |
|---|---|---|---|---|---|---|---|---|---|---|---|
| 3 | methanol | 5 | 70 | 5 | 8 | 70 | 5 | 20 | 15 | 84 | 345 |
| 4 | neutral surfactant | 1 | 60 | 5 | 8 | 70 | 5 | 20 | 15 | 126 | 523 |
| 5 | alkaline surfactant | 1 | 60 | 5 | 8 | 70 | 5 | 20 | 15 | 67 | 234 |
| 6 | neutral surfactant | 1 | 60 | 5 | 12 | 70 | 5 | 20 | 15 | 46 | 178 |
| 7 | 5% $Na_2CO_3$ | 1 | 60 | 5 | 8 | 70 | 5 | 20 | 15 | 46 | 182 |
| 8 | 5% $Na_2CO_3$ | 1 | 60 | 5 | 12 | 70 | 5 | 20 | 30 | 43 | 165 |
| 9 | neutral surfactant | 1 | 60 | 5 | 8 | 70 | 5 | 50 | 15 | 34 | 137 |
| 10 | 5% $Na_2CO_3$ | 1 | 60 | 5 | 8 | 70 | 5 | 50 | 15 | 35 | 133 |
| 11 | neutral surfactant | 1 | 60 | 5 | 8 | 70 | 5 | 200 | 2.8 | 21 | 85 |
| 12 | neutral surfactant | 1 | 60 | 5 | 8 | 70 | 5 | 200 | 1.3 | 28 | 98 |

EXAMPLES 13-16 AND CONTROL 3

A polyethylene terephthalate film 50 m in thickness (weight-averaged molecular weight 48,000) (area 50 cm²) was washed in a varying treating agent indicated in Table 2 under application of ultrasonic waves and then subjected to a drying treatment. Then, the film was immersed in a mixed solution containing the same silicon compound as used in Example 1 in a concentration of 12% by weight for a varying period indicated in Table 2, during which period the film was exposed to ultrasonic waves at a frequency of 45 KHz. Subsequently, under a varying set of drying conditions indicated in Table 2, the film was subjected to a plasma treatment twice at an output power of 200 W in the presence of oxygen of a concentration of 0.2 molar fraction. The results were as shown in Table 2. During the first and second rounds of the plasma treatment, the film was cooled for 5 minutes.

For comparison, the same film in its untreated form, was tested similarly.

TABLE 2

| Example | Pretreating Agent | Time (min) | Drying of Pretreating Temp. (°C.) | Time (min) | Dipping Time (min) | Drying Temp. (°C.) | Time (min) | Plasma reaction Time (min) | Gas permeability (ml/m² day atm) $O_2$ | $CO_2$ |
|---|---|---|---|---|---|---|---|---|---|---|
| Control 3 | — | — | — | — | — | — | — | — | 51.0 | 232.3 |
| Example 13 | 5% $Na_2CO_3$ | 1 | 80 | 15 | 15 | 80 | 30 | 1st 3 2nd 2.5 | 3.4 | 15.6 |

TABLE 2-continued

| Example | Pretreating Agent | Pretreating Time (min) | Drying of Pretreating Temp. (°C.) | Drying of Pretreating Time (min) | Dipping Time (min) | Drying Temp. (°C.) | Drying Time (min) | Plasma reaction Time (min) | Gas permeability (ml/m² day atm) O₂ | Gas permeability (ml/m² day atm) CO₂ |
|---|---|---|---|---|---|---|---|---|---|---|
| Example 14 | neutral surfactant | 1 | 80 | 15 | 5 | 80 | 30 | 1st 4.1 2nd 2.6 | 4.3 | 19.6 |
| Example 15 | none | — | — | — | 5 | 70 | 15 | 1st 3.6 2nd 3.7 | 3.8 | 17.5 |
| Example 16 | 5% Na₂CO₃ | 1 | 60 | 15 | 5 | 70 | 15 | 1st 2.6 2nd 2 | 2.9 | 13.2 |

EXAMPLE 17

By following the procedure of Example 1, a vacuum blood collection tube was obtained from a blind tube made of polyethylene terephthalate. The tube was tested similarly. The results were similar to those obtained in Example 1.

EXAMPLE 18

In a blind tube treated by following the procedure of Example 17, a culture medium of the formula shown in Table 3 was placed. The tube was tightly stoppered with a plug member made of a composition comprising of 25 parts by weight of a thermoplastic elastomer (1,2-polybutadiene), 35 parts by weight of polyisobutylene (molecular weight 100,000), 25 parts by weight of partially cross-linked butyl rubber, and 15 parts by weight of liquid paraffin, with the interior of the tube kept under a vacuum. The tube with its content was sterilized with gamma ray 1.4 Mrads in intensity. It was left standing in the atmosphere for three months. When the tube was opened at the end of the standing, the culture medium held inside was found to be free from degeneration and the degree of vacuum to be substantiallamintact.

TABLE 3

| Tryptophan | 17 g |
|---|---|
| Soybean peptone | 3 g |
| Meat extract | 3 g |
| Yeast extract | 5 g |
| Liver hydrolyzate | 1 g |
| Glucose | 2.5 g |
| Potassium hydrogen phosphate | 2.5 g |
| Sodium chloride | 5 g |
| L-cysteine hydrochloride | 0.45 g |
| P-aminobenzoic acid | 0.05 g |
| Polyanethole sulfonate sodium | 0.35 g |
| Hemin | 0.005 g |
| Agar | 0.01 g |
| Gelatin | 12 g |
| Distilled water | 1,000 ml |
| pH 7.3 ± 0.1 | |

EXAMPLE 19

A tubular container having one end thereof closed and the other end thereof opened as illustrated in FIG. 5 and measuring 1 mm in wall thickness was produced with polyethylene terephthalate. This tubular container was treated in an aqueous 5% sodium carbonate solution under application of ultrasonic waves for one hour and then dried at 60° C. for 15 minutes. Then, in a mixed solution containing the same silicon compounds as used in Example 18 in a concentration of 12% by weight, the tubular container was kept immersed for five minutes under application of ultrasonic waves at a frequency of 45 KHz. It was subsequently dried at 70° C. for 15 minutes. It was further subjected to a plasma treatment at an output power of 200 W in the presence of oxygen gas for five minutes. Consequently, there was obtained a container of synthetic resin having the outer surface thereof covered with a transparent coating 0.07 μm in thickness. In the container, culture medium of the formula shown in Table 4 was placed. The container was tightly closed with a plug member made of a composition comprising 25 parts by weight of a thermoplastic elastomer (1,2-polybutadiene), 35 parts by weight of polyisobutylene (molecular weight 100,000), 25 parts by weight of partially cross-linked butyl rubber, and 15 parts by weight of liquid paraffin, with the interior of the container kept under a vacuum. The container with its content was sterilized with gamma ray 1.5 Mrads in intensity. It was left standing in the atmosphere for three monthes. When the container was opened at the end of the standing, the culture medium held inside was found to be free from degeneration and the degree of vacuum to be substantially intact.

TABLE 4

| Tryptophan | 17 g |
|---|---|
| Soybean peptone | 3 g |
| Meat extract | 3 g |
| Yeast extract | 5 g |
| Liver hydrolyzate | 1 g |
| Glucose | 2.5 g |
| Potassium hydrogen phosphate | 2.5 g |
| Sodium chloride | 5 g |
| L-cycsteine hydrochloride | 0.45 g |
| P-aminobenzoic acid | 0.05 g |
| Polyanethole sulfonate sodium | 0.35 g |
| Hemin | 0.005 g |
| Agar | 0.01 g |
| Gelatin | 12 g |
| Distilled water | 1,000 ml |
| pH 7.3 ± 0.1 | |

EXAMPLE 20

A container made of synthetic resin obtained by following the procedure of Example 1 was used as a container for a chemical agent. The container with its content was left standing for a long time. When the container was opened after the standing, the chemical agent held inside was found to be free from degeneration.

EXAMPLE 21

A container having one end thereof closed and the other end thereof opened as illustrated in FIG. 1 and measuring 1 mm in wall thickness was produced with polycarbonate. The tubular container was treated in an aqueous 5% sodium carbonate solution under application of ultrasonic waves of a frequency of 40 KHz for five minutes and then dried at 60° C. for five minutes. Then, it was immersed in a mixed solution containing the same silicon compounds as used in Example 1 in a concentration of 32% by weight for five minutes under application of ultrasonic waves 45 KHz in frequency and then dried at 70° C. for five minutes. It was further subjected to a plasma treatment at an output power of 200 W in the presence of 100% oxygen gas for 15 minutes. Consequently, there was obtained a container of synthetic resin having the outer surface thereof covered with a transparent coating 0.14 μm in thickness. This container was filled with a transfusion fluid containing amino acid (including tryptophan) in a concentration of 12% and prepared by the ordinary method and then charged with nitrogen gas. With the interior of the container held under a vacuum, the open end thereof was sealed with a rubber plug. The container with its content was sterilized in an autoclave. The container was left standing in the atmosphere at normal room temperature for three months. When the container was opened after the standing, the content held within was found to be free from degeneration.

As described above, this invention provides a container made of synthetic resin and provided at one portion thereof with at least one tightly closable opening, which container has formed on at least either of the inner and outer surface thereof a continuous coating of a gas barrier property by the reaction of a mixture of a silicon compound having the general formula I with a silicon compound having the general formula II. Because of the coating possessed of a gas barrier property, the container exhibits extremely low permeability to gases, particularly to oxygen, so that the possible passagage of gas through the wall of the container into and out of the container interior is substantially eliminated. When this container is used for such a chemical agent as amino acid which is susceptible of oxidation, therefore, the passage of gases, particularly oxygen, into the container interior is substantially eliminated. As the result, the interior of the container can be retained under a stated pressure for a long time and the chemical agent held within can be prevented from degeneration for a long time. When this container is used for holding a gas containing beverage under high pressure, the escape of gases, particularly carbon dioxide gas, from within is notably repressed. As the result, the high pressure inside the container can be retained intact for a long time. Moreover, since the container of the present invention is made of synthetic resin, there is absolutely no possibility of the container sustaining any damage on exposure to shocks during transportation, storage, or use.

Further, this invention relies for the formation of the coating upon the action of plasma. At the same time that the coating is formed, the surface of the substrate, i.e. the wall of the container, is coarsened by the plasma. Thus, the coating is easily formed uniformly in a small thickness as deposited fast on the surface.

When the container is used for holding a chemical agent such as a fatty transfusing fluid or a nutritive drink containing amino acids which is highly susceptible to oxidation, the passage of gases, particularly oxygen, into the container interior is substantially eliminated. Thus, the chemical agent held in the container can be preserved for a long time without entailing any degeneration. When the container is used for holding such an electrolyte as glucose solution or physiological saline water, since it possesses virtually no permeability to gases, the steam rising from the electolyte is not suffered to escape from within the container interior. Thus, the electrolyte within the container is allowed to retain its original concentration intact for a long time. Further, the container of the present invention retains its extremely low permeability to gases safely even under the harsh conditions of the sterilization with high-pressure steam. The chemical agent held within, therefore, can be retained substantially intact even after the sterilization. Since the container for the chemical agent is made of synthetic resin, it has absolutely no possibility of sustaining any damage on exposure to shocks during its transportation, storage, or use.

When the container is used for holding a testing agent such as culture medium or anticoagulant which is liable to be degenerated on exposure to oxygen, since it substantially eliminates the passage of gases, particularly oxygen, into the container interior, the testing agent held within can be retained intact for a long time. Where the testing agent is in the form of an aqueous solution, the steam departing from the testing agent is not suffered to escape from the container interior and, therefore, the testing agent is allowed to retain its original concentration intact for a long time. Because of its satisfactory gas barrier property, the container can be utilized for anaerobic culture of microorganisms.

As described, this invention provides a method for the manufacture of a container made of synthetic resin and provided at one portion thereof with at least one tightly closable opening, which method comprises applying upon at least either of the inner and outer surfaces of the container body a mixed solution comprising a silicon compound having the general formula I and a silicon compound having the general formula II, drying the applied layer of the mixed solution, and subsequently subjecting the dried layer to a plasma treatment in the presence of the gas of an oxygen atom-containing molecule thereby covering the aforementioned surface of the container body with a continuous coating possessing a gas barrier property. Thus, the present invention permits ready production of a container made of synthetic resin and possessed of the aforementioned gas barrier property. Since the coating of the gas barrier property can be formed on the surface of the container body made of synthetic resin quickly at a relatively low temperature, the produced container does not suffer the container body to yield to deformation under heat or entail exudation of additives.

Further, when the application of the mixed solution upon the surface of the container body is carried out under the influence of ultrasonic waves, since the removal of air from the fine pores on the surface and the entry of the film-forming component of the solution into the fine pores are accelerated by the ultrasonic waves, the produces coating enjoys fast adhesion to the surface and the gas barrier property of this container is further improved by subjecting the container body to washing treatment particularly in an alkali bath and/or under the influence of ultrasonic waves before the application of the aforementioned mixed solution.

What is claimed is:

1. A container made of synthetic resin and provided at one portion thereof with at least one tightly closable opening, which container has on at least either of the inner and outer surfaces thereof a continuous coating having a gas barrier characteristics comprising low permeability to oxygen and carbon dioxide by the plasma treatment reaction of a mixture of a silicon compound having the general formula I:

wherein m denotes an integer of the value of 1 to 5, with a silicon compound having the general formula II:

wherein n denotes an integer of the value of 1 to 5 and $R^1$ and $R^2$ independently denote an alkyl or alkoxy group having 1 to 4 carbon atoms, a phenyl group, or hydroxyl group, providing that both $R^1$ and $R^2$ are not both hydroxyl groups.

2. A container made of synthetic resin according to claim 1, wherein the ratio of said silicon compound (II) being from 0.5 to 3 mols per mol of said silicon compound (I).

3. A container made of synthetic resin according to claim 1, wherein said container body made of synthetic resin is made of transparent synthetic resin.

4. A container made of synthetic resin according to claim 2, wherein said coating is a transparent coating.

5. A container made of synthetic resin according to claim 1, wherein said coating has a thickness in the range of 0.01 to 2 μm.

6. A container made of synthetic resin according to claim 1, wherein m in said general formula I denotes an integer of the value 1 to 5 and n in said general formula II denotes an integer of the value 1 to 5 and $R^1$ and $R^2$ in the same general formula independently denote an alkyl group having 1 to 4 carbon atoms or a hydroxyl group and the ratio of silicon compound (II) being from 1 to 2 mols per mol of said silicon compound (I).

7. A container made of synthetic resin according to claim 6, wherein $R^1$ in said general formula II is an alkyl group having 1 or 2 carbon atoms and $R^2$ in the same general formula is a hydroxyl group.

8. A container made of synthetic resin according to claim 1, wherein said container body is a tubular member made of synthetic resin and having one end thereof closed and the other end thereof opened and said open end of said tubular member is tightly closed with a pierceable plug member.

9. A container made of synthetic resin according to claim 8, wherein said container is a vacuum blood collecting vessel.

10. A container made of synthetic resin according to claim 8, wherein said container is further subjected to sterilization with radiation.

11. A container made of synthetic resin according to claim 10, wherein said radiation is gamma ray.

12. A container made of synthetic resin according to claim 8, wherein said tubular member has chemical agent for test held therein.

13. A container made of synthetic resin according to claim 12, wherein said chemical agent for test in an oxidative substance.

14. A container made of synthetic resin according to claim 13, wherein said oxidative substance is a liquid or gel-like culture medium.

15. A container made of synthetic resin according to claim 13, wherein said oxidative substance is an anticoagulant.

16. A container made of synthetic resin according to claim 8, wherein said closed space is kept under pressure lower than the atmospheric pressure.

17. A container made of synthetic resing according to claim 1, wherein said container body holds a chemical agent therein and has the opening thereof closed to isolate the inner atmosphere from the outer atmosphere.

18. A container made of synthetic resin according to claim 17, wherein said chemical agent is an oxidative substance.

19. A container made of synthetic resin according to claim 18, wherein said chemical agent is a liquid.

20. A container made of synthetic resin according to claim 17, wherein said container body made of synthetic resin is formed of synthetic resin resistant to heat.

21. A container made of synthetic resin according to claim 17, wherein said inner atmosphere is formed of a gas inactive to said chemical agent.

22. A method for the manufacture of a container made of synthetic resin and provided at one portion thereof with at least one tightly closable opening, which method comprises applying upon at least either of the inner and outer surfaces of the container body a mixed solution consisting of a silicon compound having general formula I:

wherein m denotes an integer of the value of 1 to 5, and a silicon compound having the general formula II:

wherein n denotes an integer of the value of 1 to 5 and $R^1$ and $R^2$ independently denote an alkyl or alkoxy group having 1 to 4 carbon atoms, a phenyl group, or hydroxyl group, providing that both $R^1$ and $R^2$ are not both hydroxyl groups, drying the applied layer of said mixed solution, and subsequently subjecting the dried layer to a plasma treatment in the absence of a catalyst and in the presence of the gas of an oxygen atom-containing molecule thereby covering said surface of the container body with a continuous coating having gas barrier characteristics comprising low permeability to oxygen and carbon dioxide.

23. A method according to claim 22, wherein the ratio of said silicon compound (II) is from 0.5 to 3 mols per mol of said silicon compound (I).

24. A method according to claim 22, wherein said reaction is carried out under a vacuum in the range of 0.01 to 2.0 Torrs.

25. A method according to claim 22, wherein the gas of an oxygen atom-containing molecule contains oxygen in a concentration in the range of 20 to 100%.

26. A method according to claim 22, wherein the reaction temperature is in the range of 0° to 150° C.

27. A method according to claim 22, wherein m in said general formula I denotes an integer of the value of 1 to 5 and n in said general formula II denotes an integer of the value of 1 to 5 and $R^1$ and $R^2$ in the same general formula independently denote an alkyl group having 1 to 4 carbon atoms or hydroxyl group and the ratio of silicon compound (II) being from 1 to 2 mols per mol of said silicon compound (I).

28. A method according to claim 27, wherein $R^1$ in said general formula II is an alkyl group having 1 or 2 carbon atoms and $R^2$ in the same general formula is hydroxyl group.

29. A method according to claim 22, wherein said plasma treatment is carried out for a period in the range of 0.1 to 60 minutes.

30. A method according to claim 22, wherein said synthetic resin is transparent synthetic resin.

31. A method according to claim 22, wherein said mixed solution of silicon compounds is applied on the surface of said container body by virtue of ultrasonic waves.

32. A method according to claim 22, wherein said container body made of synthetic resin is washed in advance.

33. A method according to claim 32, wherein said washing treatment is carried out in an aqueous solution.

34. A method according to claim 33, wherein said washing treatment is carried out by virtue of ultrasonic waves.

35. A method according to claim 22, wherein said container body made of synthetic resin is washed in advance and said mixed solution of silicon compounds is applied to the surface of said container body by virtue of ultrasonic waves.

36. A method according to claim 35, wherein said washing treatment carried out in an aqueous solution.

37. A method according to claim 36, wherein said washing treatment is carried out by virtue of ultrasonic waves.

38. A method according to claim 22, wherein said plasma treatment is carried out as split in a plurality of rounds.

39. A method according to claim 38, wherein said plasma treatment is carried out as split in two rounds and the container under treatment in cooled between the first and second rounds of the plasma treatment.

* * * * *

UNITED STATES PATENT AND TRADEMARK OFFICE
CERTIFICATE OF CORRECTION

PATENT NO. : 4,735,832
DATED : April 5, 1988
INVENTOR(S) : ICHIKAWA et al

It is certified that error appears in the above-identified patent and that said Letters Patent is hereby corrected as shown below: Title page item (56);

Under the "U.S. PATENT DOCUMENTS", insert the following:

```
4,599,243   7/1986    Sachdev.........427/41
4,385,086   5/1983    Nakayama et al..427/587
4,228,032  10/1980    Talcott et al...128/272
4,490,420  12/1984    Yoshida.........428/35
```

Under "FOREIGN PATENT DOCUMENTS", insert the following:

```
2443484    7/1980    France
2021976   12/1979    Great Britain
2523847    9/1988    France
```

Column 1, lines 35-36: "exmaples" should read --examples--.

Column 2, line 6: "adpoted" should read --adopted--.

Column 5, line 24:
  "atomcontaining" should read --atom-containing--.

Column 10, line 5: "exmaple" should read --example--.

Column 12, line 7: Before the formula, insert --continuous layer of--.

Column 13, line 43: "elctron" should read --electron--.

Column 16, line 16: "wasing" should read --washing--.

Column 17, lines 36-37: "substantiallamintact" should read --substantially intact--.

UNITED STATES PATENT AND TRADEMARK OFFICE
CERTIFICATE OF CORRECTION

PATENT NO. : 4,735,832
DATED : April 5, 1988
INVENTOR(S) : ICHIKAWA et al

It is certified that error appears in the above-identified patent and that said Letters Patent is hereby corrected as shown below:

Column 18, line 40: "cycsteine" should read --cysteene--.

Column 20, line 53: "produces" should read --produced--.

Column 24, line 24 (claim 39): "in" should read --is--.

Signed and Sealed this

Twenty-first Day of July, 1992

Attest:

DOUGLAS B. COMER

Attesting Officer   Acting Commissioner of Patents and Trademarks